United States Patent [19]

Harley

[11] Patent Number: 5,610,987
[45] Date of Patent: Mar. 11, 1997

[54] ACTIVE NOISE CONTROL STETHOSCOPE

[75] Inventor: Thomas R. Harley, Oxford, Miss.

[73] Assignee: University of Mississippi, University, Miss.

[21] Appl. No.: 615,166

[22] Filed: Mar. 12, 1996

Related U.S. Application Data

[62] Division of Ser. No. 106,607, Aug. 16, 1993.

[51] Int. Cl.$^6$ .............................. A61B 7/04; H04R 3/00; H04R 25/00
[52] U.S. Cl. ............................ 381/67; 381/71; 381/190; 381/114
[58] Field of Search ................................. 381/190, 114, 381/67, 71, 151

[56] References Cited

U.S. PATENT DOCUMENTS

| | | | |
|---|---|---|---|
| 2,983,790 | 5/1961 | Olson | 179/1 |
| 4,153,815 | 5/1979 | Chaplin | 179/1 P |
| 4,295,471 | 10/1981 | Kaspari | 128/675 |
| 4,435,751 | 3/1984 | Hori | 364/574 |
| 4,445,675 | 5/1984 | Kitaura | 269/20 |
| 4,473,906 | 9/1984 | Warnaka | 381/71 |
| 4,480,333 | 10/1984 | Ross | 381/71 |
| 4,489,441 | 12/1984 | Chaplin | 381/71 |

(List continued on next page.)

OTHER PUBLICATIONS

"Computational Optimization of Preditive Filter for Noise Cancellation," Abstract of 15 minute seminar presented by T. R. Harley at the 120th Meeting of the Acoustical Society of America, Nov. 26–30, 1990, *J. Acoust. Soc. Am.* Suppl. 1, vol. 88, Fall 1990, p. S39.

"DSP Control Algorithm for Canceling Broadband Random Noise with a Single Microphone and Speaker," Abstract of 15 minute seminar presented by T. R. Harley at the 122nd Meeting of the Acoustical Society of America, Nov. 4–8, 1991, *J. Acoust. Soc. Am.*, vol. 90, No. 4, Pt. 2, Oct. 1991, p. 2316.

(List continued on next page.)

*Primary Examiner*—Forester W. Isen
*Attorney, Agent, or Firm*—Bacon & Thomas

[57] ABSTRACT

An active noise control stethoscope enables a physician or paramedic to check vital signs in the presence of high background noise levels. A digital processing technique is used to remove noise from the output of a main detection sensor, the detector being impedance mismatched with air and therefore less sensitive to external airborne noise. Instead of a microphone, the detector uses a piezoceramic transflexural actuator mounted in a cylindrical piece of brass, with a polyurethane coating placed over the active side of the sensor to keep the sensor waterproof and broaden the response of the sensor. An identical sensor is placed above the device to detect background noise adjacent the device, the signals being combined to obtain a signal free of background noise. A third sensor is also used to electronically remove noise detected by the main sensor, the third sensor being positioned to pick-up noise coupled through the patient's body. The time varying voltages from signals output by these sensors are digitized and processed by the digital signal processor, and the output used to drive the speakers in the headset. The digital signal processor uses a least mean squared algorithm to digitally subtract out the part of the detector signal that is correlated to the signals from the second and third sensors. In addition, noise penetrating the earcups of the headset is reduced by using the speakers to generate antinoise. The antinoise is generated by a filtered X-adaptive digital algorithm, and also by a random noise cancellation system which sets up an infinite impulse response filter in which the coefficients are continually updated for minimizing an ear sensitivity weighted sound pressure level detected by a microphone inside the headset.

3 Claims, 3 Drawing Sheets

U.S. PATENT DOCUMENTS

| | | | |
|---|---|---|---|
| 4,490,841 | 12/1984 | Chaplin et al. | 381/71 |
| 4,494,075 | 1/1985 | Yoshihisa | 330/254 |
| 4,537,200 | 8/1985 | Widrow | 128/696 |
| 4,596,033 | 6/1986 | Swinbanks | 381/71 |
| 4,644,581 | 2/1987 | Sapiejewski | 381/74 |
| 4,673,982 | 6/1987 | Tam et al. | 455/295 |
| 4,677,677 | 6/1987 | Eriksson | 381/71 |
| 4,783,814 | 11/1988 | Foley | 381/67 |
| 4,784,154 | 11/1988 | Shirley et al. | 381/67 |
| 4,856,118 | 8/1989 | Sapiejewski | 2/209 |
| 4,947,435 | 8/1990 | Taylor et al. | 381/71 |
| 5,033,082 | 7/1991 | Eriksson | 379/410 |
| 5,161,200 | 11/1992 | Barr | 381/190 |
| 5,181,252 | 1/1993 | Sapiejewski | 381/187 |
| 5,182,774 | 1/1993 | Bourk | 381/72 |
| 5,196,755 | 3/1993 | Shields | 310/324 |
| 5,209,237 | 5/1993 | Rosenthal | 128/698 |
| 5,251,263 | 10/1993 | Andrea et al. | 381/71 |
| 5,305,387 | 4/1994 | Sapiejewski | 381/72 |
| 5,321,761 | 6/1994 | Kitanishi | 381/114 |

OTHER PUBLICATIONS

Widrow & Stearns, Adaptive Signal Processing, 1985, pp. 154–161 and 288–295.

Ericksson, L. J., "Recursive Algorithms for Active Noise Control," Int. Symposium on Active Control of Sound and Vibration, Apr. 1991, pp. 137–146.

Widrow, Bernard, et al., "Adaptive Noise Cancelling Principles and Applications" Proc. TEEE, Vol. 63, No. 12, Dec. 1975, pp. 1692–1716.

Elliott, S. J. and Nelson, P. A., "Active Noise Control," IEEE Signal Processing Magazine, Oct. 1993, pp. 12–35.

(SPEAKER)
$S_e$ = (unwanted) sound external to earcup
$S_i$ = (unwanted) sound inside earcup 5,610,987

ACTIVE NOISE CONTROL STETHOSCOPE

This invention was made with government support under Contract No. DAMD 17-93-C-3088 awarded by the Department of the Army and Contract No. N61331-91-C-0013 awarded by the Department of the Navy. The government has certain fights in the invention.

This application is a division of application Ser. No. 08/106,607, filed Aug. 16, 1993.

BACKGROUND OF THE INVENTION

1. Field of the Invention

This invention relates to the field of active noise control, and in particular to an electronic stethoscope usable in a noisy environment.

2. Description of Related Art

Use of a stethoscope for auscultation, for example to detect lung noises or monitor heart beats, is often impossible in ambulances, medivac helicopters, and other emergency medical environments due to detection of extraneous noise and vibrations by the sensing device of the stethoscope, and because the signal output by the sensing device must compete with additional airborne noise that penetrates past the earpiece of the stethoscope and into the user's ear. In order to solve the problem of auscultation in a noisy environment, the stethoscope must limit both the direct detection of extraneous sounds by the sensing device of the stethoscope and the effect of noise which penetrates past the earpiece of the stethoscope. No such system currently exists, although solutions have been achieved for specialized situations. Such solutions have generally involved substituting an electrical transducer such as a piezoelectric microphone element for the vibration detector of a conventional stethoscope, and then applying electronic signal processing techniques to the resulting electrical signal.

There are several advantages to having a sensor with electronic output. First, the electronic output is amenable to filtering in order to receive the frequency band of interest. Thus, noise outside the frequency band of interest can be removed. Second, heart and lung sounds often get garbled by reverberation in the rubber tubes of conventional stethoscopes, but the electronic signal produced by the electronic sensor is not susceptible to such reverberations. Third, a sensor that generates an electronic signal is advantageous in that the electronic signal can be amplified and filtered to compensate for hearing loss specific to an individual physician. Finally, the electronic signal generated by the sensor can be used in conjunction with adaptive noise control techniques to further reduce unwanted noise.

The earliest forms of electronic signal processing in this context involved adaptive noise cancellation techniques based on subtraction of reference signals related to specific noise sources. For example, a DSP implementing a least means squared (LMS) algorithm was successfully used to remove unwanted 60 Hz noise which interfered with the recording of electrocardiograms (ECGs). For this application, the primary input signal was the ECG, which was correlated with a secondary input reference signal taken from a nearby electrical power outlet in order to obtain the part of the primary signal uncorrelated with the 60 Hz source of electrical interference.

In another application of the LMS filtering technique, a fetal ECG device was developed which cancelled out maternal heartbeat sounds from a fetal heartbeat stethoscope. For this application, the primary signal came from a stethoscope placed near the infant, and the secondary reference signal was obtained from a stethoscope near the mother's heart. After removing the part of the primary signal correlated with the reference signal, the infant's heartbeat could be heard much more clearly.

More recently, rather than relying only on passive attenuation of external noise, research has focused on active noise control techniques. Here, active noise attenuation refers to the reduction of noise due to interference with a controlled secondary source of sound or "antinoise". No matter how noise-free the speaker's output, external airborne noise which penetrates to the listener's eardrum will still be a problem. In the case of a stethoscope, for example, external airborne noise that penetrates to the listener's eardrum and masks the relevant stethoscope signal can significantly interfere with the listener's interpretation of the signal. Since the source of noise does not come from the speaker driving signal, it cannot be controlled by simply passively filtering the speaker driving signal, but rather must be actively controlled.

The active control of sound in antinoise headsets is currently being investigated by many researchers. This headset research is divided between work using analog devices and digital (DSP) devices. Analog headsets have been under development for some time (see U.S. Pat. No. 4,445,675, and also U.S. Pat. Nos. 4,494,075, 4,644,581 and 4,856,118) and currently more than ten companies, including The Bose Corp., have made such headsets commercially available. Basic research on the design of DSP anti-noise headset systems is currently on-going. While the analog systems are less expensive, their cancellation performance is limited.

Unlike analog systems, a digital antinoise system can adaptively redefine its operating parameters in order to seek out the optimal way to cancel a particular noise problem. However, in practice, most DSP algorithms only remove periodic noise in ANC headsets. Periodic noise is much easier to cancel than broadband random noise. In emergency medical environments where most of the noise is periodic, the conventional algorithms are satisfactory. Nevertheless, there are many situations in which random noise cancellation is required.

Even where the external noise source is periodic, active noise control techniques by themselves may be inadequate to completely eliminate the background noise. Problems include inadequate reference sources for attenuation of both electronic noise in the primary signal and acoustical noise near the ear of the stethoscope's user, a primary signal which is too weak in relation to the noise sources, and differences in sound between the electronically filtered speaker output and the sound to which the user is accustomed. The present invention seeks to provide complete solution to these and other problems by using a variety of electronic processing techniques and by combining these signal processing improvements with improvements in the hardware by which the electrical signals to be processed are obtained.

SUMMARY OF THE INVENTION

It is a first objective of the invention to provide an electronic stethoscope that enables emergency medical personnel to auscultate in the presence of a high background noise level, by providing an improved primary signal sensor and an optimized combination of both passive and active noise cancellation technology in order to increase the signal-to-noise ratio of the signals output to drive a headset speaker, and reduce the effect of external airborne noise which can mask sounds output by the headset speaker.

It is a second objective of the invention to provide an active noise cancellation (ANC) or active noise reduction (ANR) system capable of cancelling random as well as periodic noise.

These objectives are accomplished in part by a unique detection sensor for picking up sound from the patient directly, in which the transducer has an impedance which is matched to that of human flesh rather than with the air, and therefore is much less sensitive to external airborne noise than commercial electronic stethoscopes with conventional microphones having very light diaphragms designed to minimize the impedance mismatch with air.

In an especially preferred embodiment of this aspect of the invention, the detection sensor is a piezoelectric transflexural actuator, designed to be excited by lung and heart sounds when in contact with the patient and produce an electric signal representative of the lung and heart sounds with no external power.

The objectives of the invention are further accomplished by providing additional sensors for electronically removing noise that the first sensor detects, all three sensors outputting time varying electronic signals, which are subsequently digitized and processed by a digital signal processor used to drive speakers in the headset.

In an especially preferred embodiment of the invention, the second sensor is used for measuring airborne noise in the vicinity of the main detection sensor and the third sensor is placed away from the lungs and heart on the patient's body so that these sounds will not get subtracted out from the first sensor, the third sensor measuring sound and vibrations, e.g., from a stretcher, that have already coupled into the patient's body.

According to another aspect of the invention, the digital signal processor uses an LMS algorithm, capable of cancelling random noise, to digitally subtract out the part of a first sensor signal that is correlated to the signals from second and third sensors.

According to yet another aspect of the invention, the digital signal processor is also used to calculate a correct manner to drive the speaker to make antinoise, in order to cancel sound penetrating the earcup so that only sound corresponding to the digitally processed first sensor signal is heard in the earcup, the antinoise reference source including, if necessary, two microphones to better account for movement of the user's head and varying noise levels.

Finally, the preferred embodiments of the invention also provide for processing of the filtered sensor output to make the effects of electronic processing transparent to the user so that the sounds generated thereby mimic those produced by the conventional stethoscope to which most medical personnel are accustomed.

It will be appreciated by those skilled in the art that many features of the invention, including the novel random noise cancelling algorithm, may be used in an active control headset for purposes other than auscultation. For example, such a headset can feed through electronically transmitted communications from a radio, while cancelling unwanted noise. This might be used by a person operating a lawnmower or other noisy equipment to hear radio broadcasts, or by a person driving a military tank in a noisy battle to hear electronically transmitted commands.

Another possible application is to configure the preferred stethoscopes for use by a plumber to detect leaks in long underground pipes. Digging up long pipes is expensive, time consuming, and scars the land, so detection of leaking water using a stethoscope can be highly advantageous. However, because pipes often are laid alongside busy roads, noise can be a significant problem. Similarly, the preferred stethoscopes could be used to hear termites in wood and insects inside fruit and grain, even in environments which are otherwise prohibitively noisy, on a larger scale than is possible with random sampling.

DETAILED DESCRIPTION OF THE PREFERRED EMBODIMENTS

Figure 1:
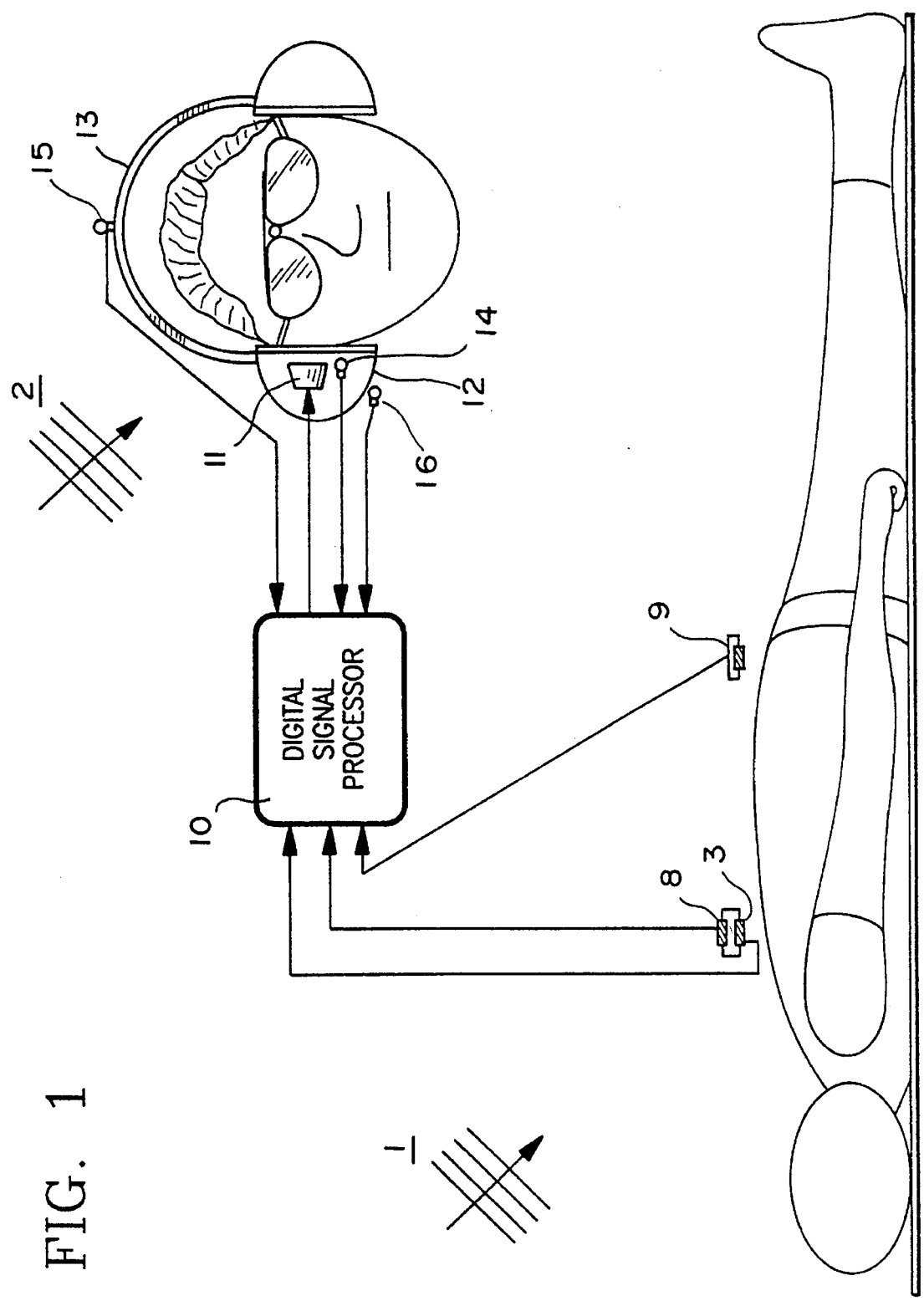
FIG. 1 is a schematic diagram of the principal components of an active noise control stethoscope arranged according to principles of a preferred embodiment of the invention.

FIG. 1 is a schematic diagram of the principal components of an active noise control stethoscope constructed in accordance with the principles of a preferred embodiment of the invention.

The two background noise sources which interfere with sound produced by a patient are indicated in FIG. 1 by the reference numerals 1 and 2. These sources are the background noise 1 in the vicinity of the patient and the background noise 2 in the vicinity of the headset.

Figure 2:
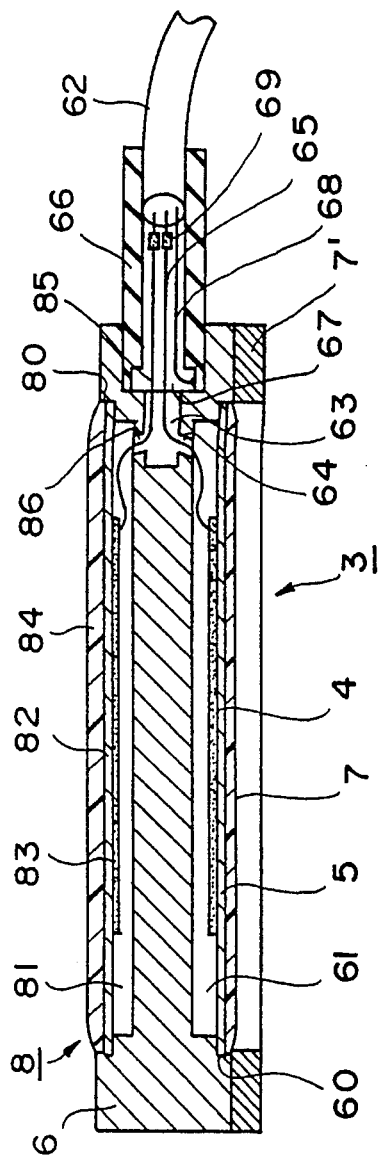
FIG. 2 is a perspective view of a piezoelectric sensor for use in the stethoscope of FIG. 1.

In order to minimize detection of noise source 1, main sensor 3, which is placed against the patient's body for directly sensing sounds originating therein, has an impedance matched with that of human flesh and mismatched with that of air, so that it is less sensitive to external airborne noise. Instead of a conventional microphone, the preferred main sensor 3 uses a piezoceramic transflexural actuator consisting of a thin layer of piezoelectric material 4 bonded to a thin conductive metal disc 5, which in turn is bonded to a conductive metal cylinder or housing 6 as shown in FIG. 2. Such piezoelectric transflexural disks are manufactured, for example, by Murata Erie North America, Inc. (part No. 7NB-41-25DM-1).

A polyurethane coating or potting 7, for example CONATHANE™ manufactured by Conap, is placed over the active side of this circular flat sensor so that when placed in contact with the patient, the polyurethane coating serves to keep the sensor waterproof and broaden the response of the sensor. Without the polyurethane coating, the piezoceramic sensor would have a sharp resonance frequency, and the physician would only hear a narrow frequency band of the sound in the patient's body. The coating 7 and a gasket 7' conduct heat slowly, and prevent contact of the patient with the metal parts of the sensor, which might otherwise feel uncomfortably cold.

The cylinder or housing 6 is preferably made of brass and includes a first cylindrical cavity 60 to which is attached the perimeter of the circular piezoceramic device by applying a thin layer of conductive epoxy and radio service cement around the perimeter of the cavity ledge. Behind the piezoceramic transflexural element made up of piezoelectric material 4 and metal disc 5 is a second cylindrical cavity 61 which allows the sensor to be displaced back and fourth. As illustrated, the brass housing 6 is wider than the piezoceramic element and metal disc 5 so that when pressed against the patient, the housing closes any direct path for airborne noise to reach the sensor.

In order to connect a shielded cable 62 to the sensor, a cavity 67 is drilled into the side of the cylinder, with an extension 63 and 64 permitting a fine insulated wire 65 to be fed to the piezoceramic disc 4. A metal tube 66 is preferably provided to anchor cable 62 and is dimensioned to fit snugly within a cavity 67 in communication with cavity 63 in order to provide a path to ground via wire 68. A wire from the cable is soldered at 69 to another wire 65. The wire 65 is preferably very thin to avoid transmitting wire vibrations to the sensor which could cause voltage fluctuations.

An identical second sensor, sensor 8, is placed adjacent the first sensor 3. For example, in the illustrated embodiment, sensor 8 is integrated into housing 6 by providing symmetric cavities 80 and 81, metal disc 82, piezoceramic disc 83, polyurethane potting 84 and connecting wire 85 in extension 86 of cavity 63, although sensor 8 could also be provided separately. For purposes of providing a reference signal for noise cancellation, sensor 8 must be placed near the point where the stethoscope makes contact with the patient, but not in contact with the patient's body, so that it measures only the external noise 1 in the vicinity of the main sensor, rather than sounds made by the patient's body itself. A third identical sensor 9 is placed on the patient's body away from the source of the sounds of interest to the physician or paramedic using the stethoscope, generally the patient's heart and lungs, in order to detect background sounds which have coupled to the patient's body, for example through a stretcher.

In a variation of the above, sensor 8 may be in the form of a small conventional microphone rather than a piezoceramic transflexural actuator. Although such a microphone would be more susceptible to external airborne noise in the vicinity of the stethoscope sensor, the substitution alleviates the problem of loud noises being created when sensor 8 is accidentally tapped. The increased susceptibility to external noise can be alleviated by filtering the output of the microphone to detect only those frequency bands detected by the main sensor 3.

Sensors 8 and 9 serve as reference signal sources for electronically removing by cancellation noise that main sensor 1 detects. The time varying voltages output by sensors 8 and 9 are digitized and processed by digital signal processor (DSP) 10, as will be described in more detail below, the output being used to drive the speakers 11 (only one of which is shown) in the earcups or earmuffs 12 of a helmet or headset 13. The digital signal processor 10 uses an LMS algorithm to correlate the detector signal from sensor 3 with the signals from sensors 8 and 9, which can then be subtracted to remove the effects of the background noise detected by those sensors. A description of a suitable LMS algorithm may be found in Widrow and Steams, *Adaptive Signal Processing*, Prentice Hall Inc., 1985, pages 288–294, 303, and 329–337.

It will of course be appreciated by those skilled in the art that each of sensors 8 and 9 can be placed in different locations depending on the nature of the background noise, and that additional sensors could be added if required. As noted above, sensor 9 is better for measuring sound and vibrations that have already coupled into the patient's body while sensor 8 measures airborne noise 1. For a typical application, it may turn out that signals from sensor 8 are strongly correlated to the noise that sensor 3 picks up, while signals from sensor 9 are not, in which case, sensor 9 may be omitted. Similarly, in another type of environment, the device might work just as well after removing sensor 8, relying only on sensor 9.

Cancelling noise picked up by the main detection sensor 1 is only one aspect of the noise problem. Noise source 2 penetrating an earcup 12 of the helmet or headset 13 worn by the physician or paramedic also interferes with the intelligibility of the filtered signal broadcast by the speaker 11 in the earcup 12, and therefore DSP 10 is also used to calculate the correct manner to drive the speaker 11 to make antinoise. While the earcup 12 of the headset 13 physically attenuates external noise which would otherwise reach the physician's ear, this attenuation is insufficient, especially at low frequencies. In the case of periodic noise, a conventional filtered-X algorithm may be used to cancel periodic noise in the earcup. An example of this known algorithm is described in the Widrow and Steams text cited above, and involves updating the coefficients of a finite impulse response (FIR) filter for processing a primary signal based on input from a microphone 15, or optionally from a second microphone 16, positioned external to the earcup 12 but adjacent the user's head, each time a sample is taken, in order to minimize an error signal representative of the total sound present in the earcup as detected by microphone 14, after the DSP has modified this signal from microphone 14 by removing the part of this signal caused by adding the stethoscope signal resulting from sensors 3, 8, and 9 to the headset antinoise speaker driving signal.

Using a single microphone 15 for input to cancel noise in the left and right earcups may be an inadequate compromise for some applications, in which case two microphones, each positioned near one of the earcups (as microphone 16) will typically provide better performance while adding some cost to the system.

Since the filtered-X algorithm is dependent on the output of microphones 14 and 16 having a cross-correlation over a finite time delay, from which one obtains a prediction of future time dependent noise levels from past data, it is best suited for periodic (repetitive or cyclic) noise which is more predictable. For generating random antinoise, a novel approach relying on auto-correlation of the output of microphone 14 to obtain updated coefficients that define the digital filter is used. As described below, the novel approach involves a numerical calculation of the constrained minimum of a function of many variables in the frequency domain. It is noted that a frequency domain calculation for active noise control was described by Ross in U.S. Pat. No. 4,480,333, but the frequency domain calculation of Ross was used for the cross-correlation of reference and error microphone signals and is not directly relevant to the preferred single microphone approach.

Figure 3:
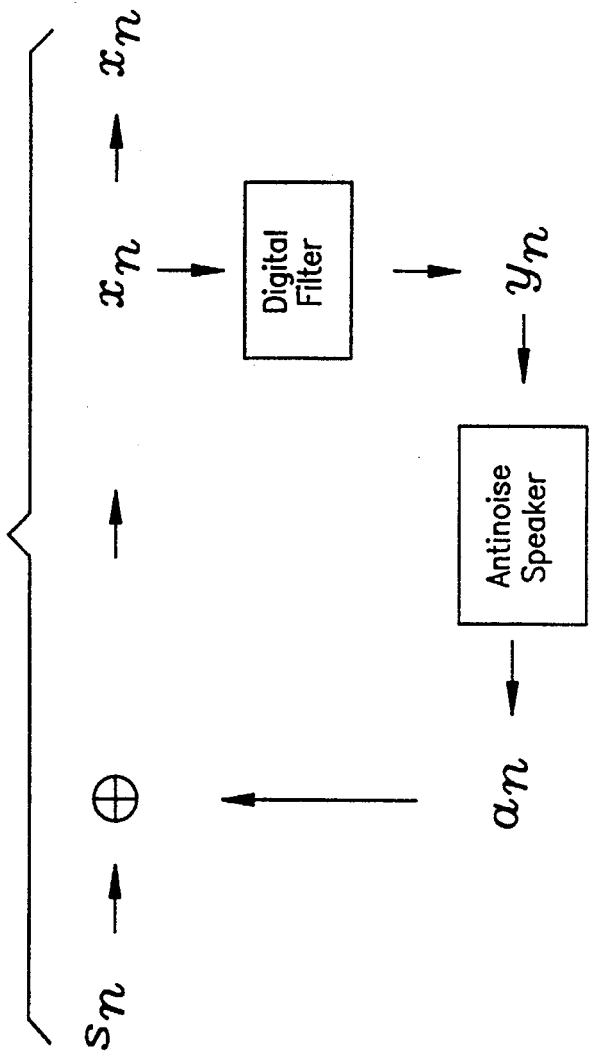
FIG. 3 is a schematic diagram illustrating the principles of antinoise generation.

The variables involved in the preferred random noise control algorithm are illustrated in FIG. 3. As shown therein, the quantities $s_n$, $a_n$, and $x_n$ are in units of microphone voltage and $y_n$ gives the driving voltage of the speaker. These quantifies are digitized at the sampling rate of DSP 10.

The variable $x_n$ to be minimized represents the total noise detected by the microphone when its signal is sampled during the nth iteration, and is the sum of the antinoise, $a_n$, and the unwanted source noise, $s_n$. In the material that follows, the term response refers to the digital impulse response of an antinoise speaker in each earcup 12. This response is given by $$\{R_n\}_{n=0}^m \quad (1)$$

which represents sample data measured by the microphone 14 when the antinoise speaker is driven by a digital impulse.

This digital impulse is defined to be $y_{-1}=1$ and $y_n=0$ for $n \neq -1$. The impulse response is truncated after $m+1$ points as it is assumed that for $n>m$, $R_n$ is negligibly small. For $n<0$, $R_n=0$ because causality applies, and delays in the system prohibit an instantaneous response. The response is used to mathematically model the antinoise speaker of FIG. 3 as a finite impulse response (FIR) digital filter with input $y_n$. The coefficients of the antinoise digital filter are given by $$\{c_k\}_{k=1}^J \text{ and } \{b_k\}_{k=0}^L \quad (2)$$

The following equations therefore describe the system illustrated in FIG. 3:

$$x_n = a_n + s_n \quad (3)$$

$$y_n = \sum_{k=1}^{J} c_k y_{n-k} + \sum_{k=0}^{L} b_k x_{n-k} \quad (4)$$

$$a_n = \sum_{k=0}^{m} R_k y_{n-k-1} \quad (5)$$

Equation 3 equates the total sound with the sum of the antinoise and unwanted source noise. Equation 4 defines the digital filter, and Equation 5 defines the "FIR filter" used to model the effect of the antinoise speaker.

When the system is initially turned on, no effort is made to cancel noise while the antinoise speaker is driven by a series of digital impulses. Many responses are recorded and subsequently averaged into a single set of response data. After performing this calibration, the response is known. The response can also be continuously updated using an "on-line" technique, although the presently preferred embodiment is to calibrate initially.

Once the response is known, the theoretical performance of the digital filter can be determined mathematically by computationally searching through the multidimensional parameter space of all possible filters defined by $$\{c_k\}_{k=1}^J, \{b_k\}_{k=0}^L \quad (6)$$

for the filter that has the most desirable frequency-dependent gain. The method of finding the coefficients that define this digital filter begins by choosing coefficients so as to minimize $\mathcal{L}$, the ear sensitivity weighted sound pressure level (SPL). Equations 7-12 define the mathematical model for $\mathcal{L}$.

$$\mathcal{L} = \int_0^\infty P(f) W(f) \, df \quad (7)$$

$$W(f) = 10^{[-M(f)+E(f)]} \quad (8)$$

$$P(f) = |T(f)|^2 P_s(f) \quad (9)$$

$$P_s(f) = \lim_{T \to \infty} \frac{|\hat{p}_s(T,f)|^2}{T} \quad (10)$$

$$\hat{p}_s(T,f) = \int_{-T}^{T} p_s(t) e^{2\pi i f t} \, dt \quad (11)$$

$$T(f) = \frac{1 - \sum_{k=1}^{J} c_k e^{[2\pi i k f/f_d]}}{1 - \sum_{k=1}^{J} c_k e^{[2\pi i k f/f_d]} - \sum_{k=0}^{L} \sum_{j=0}^{m} b_k R_j e^{[2\pi i (k+j+1) f/f_d]}} \quad (12)$$

The weighting factor, $W(f)$ is defined in Equation 8 and is a function of $M(f)$, which is used to remove the frequency dependent sensitivity of the microphone, and of $E(f)$, which describes the frequency dependent sensitivity of the human ear. A variety of options exist for determining $E(f)$, including A-weighting, an equal loudness contour (see Kinsler et al., *Fundamentals of Acoustics*, 3rd Edition, Wiley, N.Y., p. 262 (1982)), and the frequency dependent ear sensitivity weighting suggested by Stevens in "Perceived Level of Noise by Mark VII and Decibels (E)", *J. Acoust. Soc. Am.* 51, p. 575 (1972). $M(f)$ can be set to a constant for a conventional microphone with a sufficiently flat frequency response.

The unwanted source noise measured by the microphone 14 is given by $p_s(t)$, the continuous signal from which $s(n)$ is sampled. Equation 11 indicates that the truncated Fourier transform of $p_s(t)$ over a time window of $2T$ is denoted by $\hat{p}_s(T,f)$. Equation 9 defines $P(f)$, the power spectrum of the total noise when the antinoise system is running. Equation 10 indicates how the power spectrum of the random source noise, $P_s(f)$, can be estimated for large values of $T$. Equation 12 defines $T(f)$, the steady state transfer function of the antinoise model of FIG. 3. Finally, the quantity $f_d$ in equation 12 is the digitizing frequency, or the sampling rate of the digital filter. Thus, for an input source noise at a frequency $f$, $T(f)$ gives the ratio of the total noise amplitude divided by the source noise amplitude. The discrete Fourier transform convention used here is that oscillations at a single frequency $f$ vary like $\exp[-2\pi i n f/f_d]$.

The existence of a pole of $T[f]$ in the upper half complex frequency plane ($\text{Imag}(f)>0$) indicates that the antinoise system is unstable. However, the transfer function, $T(f)$, is correct for a closed loop digital system, neglecting only variations between sample points. Thus, the mathematical model has neglected the transfer functions of the "sampling" A/D and "zero order hold" D/A converters. As the sampling frequency becomes large, the errors vanish. Similar errors arise because the acoustical spectrum of the noise is calculated from digitized microphone input over a finite time window, but the errors are also found in practice to be negligible.

The dominant source of error between the mathematical model and the physical system is due to errors in the calibration of the response. To minimize these errors, DC offsets in the microphone may be eliminated by making half of the inputs positive and the other half negative, with the negative impulses being averaged in after negating the microphone signal. Preferably, high precision 12 bit A/D and D/A converters accurate to 1 part is 4096 are used and checks are made that the signals use a significant fraction of the dynamic range.

After choosing a starting point in the digital filter parameter space, a second DSP running in parallel with the DSP discussed above is used to approximate the functional value, gradient and hessian of the ear sensitivity sound pressure level $\mathcal{L}$. In the illustrated embodiment, the data is synthesized into an approximation of the integral using the trapezoidal rule, although it will be appreciated by those skilled in the art that a variety of other approximation techniques, such as Simpson's rule, may be used. The second DSP then uses a modified Newton's method to find a minimum, applying the current values for $$P_s(f) \text{ and } \{R_k\}_{k=0}^m$$

thus fleeing the first DSP from the burden of updating each filter coefficient. Analytical expressions of the first and second derivatives of $\mathcal{L}$ with respect to the filter coefficients are easily calculated, and this is exploited by choosing a faster optimization algorithm which uses this higher order information about $\mathcal{L}$. This particular hessian matrix has many symmetry properties which can be used to avoid duplicate calculations and greatly reduce the computational time required to evaluate the hessian.

The hessian of a function of many variables is defined by H as follows:

$$\text{Given } \vec{\delta} = (\delta_1, \delta_2, \ldots, \delta_p) \text{ and } \vec{\delta}^T \equiv \begin{pmatrix} \delta_1 \\ \delta_2 \\ \cdot \\ \cdot \\ \cdot \\ \delta_p \end{pmatrix}, \text{ then}$$

$$f(\vec{x}) = f(x_1, x_2, \ldots x_p), \nabla f \equiv \left( \frac{\partial f}{\partial x_1}, \frac{\partial f}{\partial x_2}, \ldots, \frac{\partial f}{\partial x_p} \right), \quad (13)$$

and given the elements of matrix $H$, $H_{ij} \equiv \frac{\partial^2 f}{\partial x_i \partial x_j}$, then for sufficiently small $\delta$, one can approproximate $$f(\vec{x} + \vec{\delta}) \approx f(\vec{x}) + \vec{\delta} \cdot \nabla f + \frac{1}{2} \vec{\delta} \cdot H \vec{\delta}^T \quad (14)$$

At marginal stability, T(f) is infinite for some real value of f. Therefore, one might expect the value of $\mathcal{L}$ to be infinite when evaluated on the boundary of stable regions in digital filter parameter space. But the introduction of the ear sensitivity weighting truncates any contribution from modes that are unstable at frequencies above 20 kHz. Further, no instabilities can occur above the Nyquist frequency of the DSP, which is typically less then 20 kHz, and the use of analog low pass filters with cutoffs below 20 kHz greatly reduces the probability of the system going unstable above the cutoff frequency. Therefore, when using only the constraint that the digital filter be stable, the minimization of $\mathcal{L}$ is an unconstrained minimization problem.

Applying the constraint of stability alone to the mathematical minimization problem can result in the design of a digital filter that makes the physical system feedback unstable. This can happen because there are differences between the computed response and the actual, current response of the physical system. Those skilled in the art will appreciate that if the feedback control system is cancelling noise well, then the controller is operating a filter with high gain. This results in the apparent paradox that the optimal digital filter can be very close to being feedback unstable.

In order to provide additional protection against instabilities, it is preferable to set a minimal transient decay rate, d, which can be tolerated by the antinoise system. Thus, the more stringent constraint of relative stability is imposed instead of an absolute stability. Each time $\mathcal{L}$ is evaluated, a check is made for insufficiently damped modes using, for example, the Routh-Hurwitz technique (those skilled in the art will appreciate that other stability tests, such as the Jury stability test, may also be adapted to make this check). If such a mode exists, an extremely large "penalty" factor is added to $\mathcal{L}$. This prevents the minimization search from converging to a point in the digital filter parameter space where transients will, theoretically, linger longer than a maximal half-life $\gamma = \ln2/d$.

The output of the filter effectively reduces the overall noise level by lowering the peaks and raising the valleys of the weighted noise source, resulting in a residual spectrum which more closely resembles white noise. White noise is known to create much less psychological irritation than unbalanced non-white noise spectra.

The intelligibility of the audio signal may optionally also be enhanced by inverting the stethoscope signal sent to one of the speakers. This effect, known as the binaural masking level difference (BMLD) enhances the ability of the physician to hear a signal that is 180° out of phase in each ear.

Figure 4:
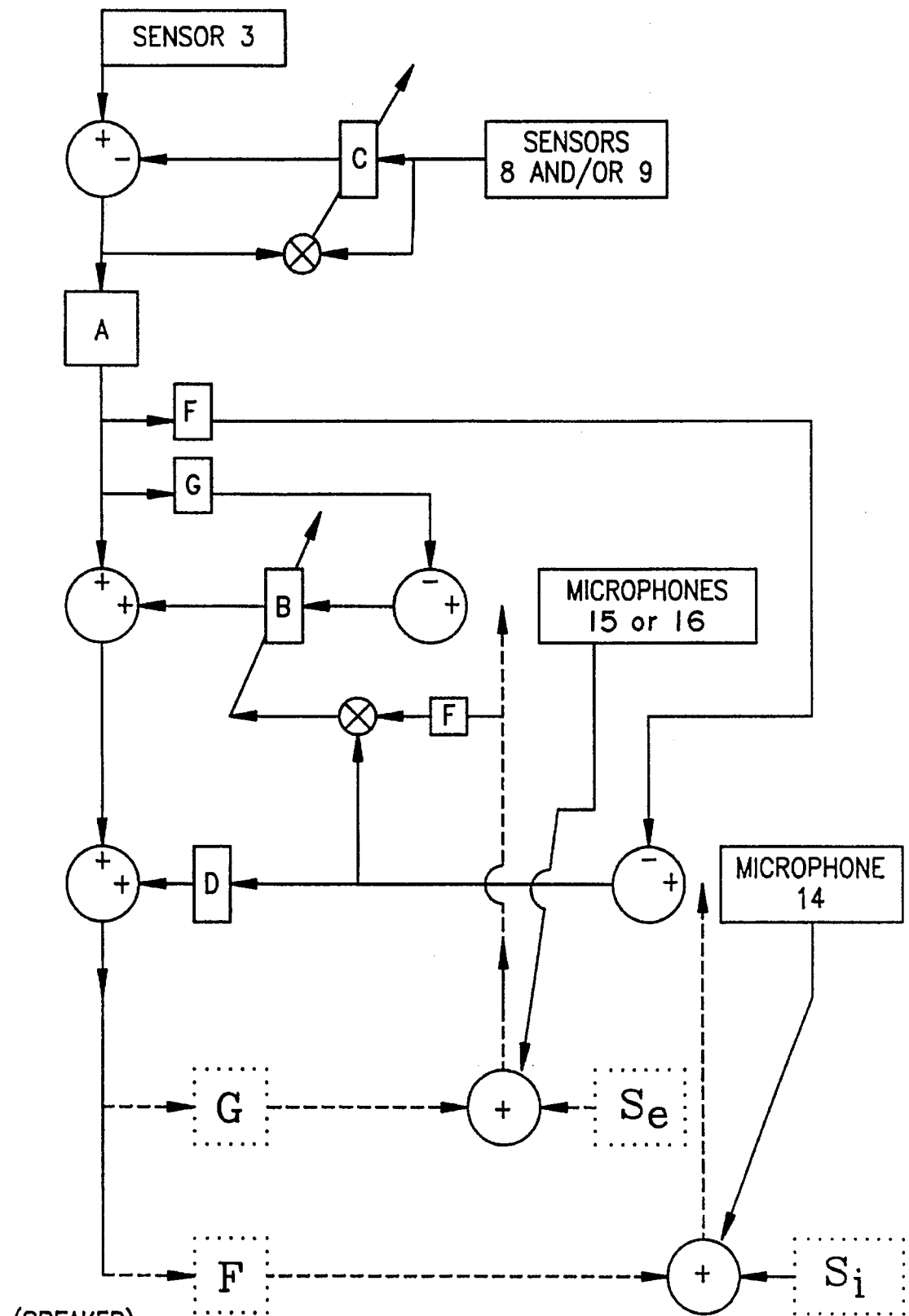
FIG. 4 is a block diagram of the processor of FIG. 1.

FIG. 4 summarizes the above-described preferred processing sequence for taking data from sensor 3, sensors 8 and/or 9, microphone 14, microphone 15, and optionally microphone 16, and sending the output to speaker (or speakers) 12. Block C represents the FIR filter that is being adaptively defined in order to remove the contribution to the stethoscope signal that is correlated to sensors 8 and/or 9. The diagonal arrow indicates the error signal being used for the LMS adaptation algorithm.

Block A represents the symmetric FIR filter used to low pass filter, amplify, and make the electronic stethoscope sound like a conventional stethoscope. The latter function is provided because, if the voltage from the electronic sensing device were used to directly drive a speaker near the physician's ear, the preferred electronic stethoscope would produce different sounds from a conventional stethoscope. This would occur even when excited by the same stimulus because the electronic stethoscope is constructed from materials different from a conventional stethoscope, and would be disturbing to medical personnel with training and experience in interpreting sounds from conventional stethoscopes. Using standard methods, however, an audiologist can determine the frequency dependent audio amplification required to make the electronic stethoscope sound like a conventional stethoscope. Techniques for using a digital signal processor to implement a digital filter with a specified frequency dependent gain are well known, the gain of the filter being adjusted by appropriate adjustment of the FIR coefficients in the same digital filter which is also used as a low pass filter and amplifier. In addition the electronic signal can be filtered and amplified to compensate for hearing loss specific to an individual physician.

Block F represents the FIR filter given by the digital response of microphone 14 to a digitized impulse on the speaker. Similarly, block G represents the FIR filter giving the impulse response of microphone 15. A corresponding additional block (not shown) would be used for microphone 16. Bloch G and F are used to subtract the contribution from the transmitted stethoscope signal out of microphones 14 and 15, preferably with the simplifying assumption that G=0 in the case where the earcup has sufficient passive attenuation of external noise, which is typical. Finally, block B represents the FIR filter that is adaptively adjusted in order to cancel periodic noise in the headset using the filtered X algorithm and block D represents the IIR digital filter defined by the preferred random noise cancelling technique.

Having thus described a specific embodiment of the invention in detail, it will be appreciated that modification and adaptations of the invention may be made without departing from the spirit or scope of the invention. Consequently, it is intended that the invention not be limited by the above description, but rather that it be defined solely by the appended claims.

I claim:

1. An electronic stethoscope, comprising:
   sensor means, including a piezoceramic transflexural actuator made up of a thin layer of piezoelectric material bonded to a thin conductive metal disc, for detecting sound exclusively from a patient and converting said sound to an electrical signal, said sensor means having an impedance which substantially matches that of a surface of the patient's body contacted by the sensor means and which is substantially different than that of air,
   wherein said conductive metal disc is bonded to a conductive metal cylindrical housing which closes any direct path by which airborne noise can reach the piezoelectric element, said housing including a first cylindrical cavity to which is attached the perimeter of the circular piezoceramic device and a second cylindrical cavity which allows the sensor to be displaced back and forth, and further comprising a waterproof insulating coating which covers the piezoceramic transflexural actuator for broadening a resonance frequency of the sensor means.

2. An electronic stethoscope as claimed in claim 1, wherein said waterproof coating is made of polyurethane.

3. An electronic stethoscope as claimed in claim 1, further comprising a second sensor means for primarily sensing background sounds and not said sound from the patient and converting said background sounds to a second electrical signal, said second sensor means comprising a second piezoelectric transflexural actuator bonded to an opposite end of the housing from the end to which the first piezoelectric transflexural actuator is bonded.

* * * * *